(12) United States Patent
Yu (10) Patent No.: US 11,992,731 B2
(45) Date of Patent: May 28, 2024

(54) AI MOTION BASED SMART HOMETRAINING PLATFORM

(71) Applicant: MULTICS CO., LTD., Daejeon (KR)

(72) Inventor: Seung-Su Yu, Daejeon (KR)

(73) Assignee: MULTICS CO., LTD., Daejeon (KR)

( * ) Notice: Subject to any disclaimer, the term of this patent is extended or adjusted under 35 U.S.C. 154(b) by 114 days.

(21) Appl. No.: 17/967,965

(22) Filed: Oct. 18, 2022

(65) Prior Publication Data

US 2024/0123287 A1  Apr. 18, 2024

(51) Int. Cl.

| A63B 24/00 | (2006.01) |
|---|---|
| A63B 71/06 | (2006.01) |
| G06T 7/246 | (2017.01) |
| G06T 11/00 | (2006.01) |
| G06V 10/774 | (2022.01) |
| G06V 40/20 | (2022.01) |
| G16H 15/00 | (2018.01) |
| G16H 20/30 | (2018.01) |

(52) U.S. Cl.
CPC ...... *A63B 24/0075* (2013.01); *A63B 71/0622* (2013.01); *G06T 7/251* (2017.01); *G06T 11/00* (2013.01); *G06V 10/774* (2022.01); *G06V 40/23* (2022.01); *G16H 15/00* (2018.01); *G16H 20/30* (2018.01); *A63B 2024/0068* (2013.01); *A63B 2071/0625* (2013.01); *A63B 2071/0647* (2013.01); *A63B 2071/068* (2013.01); *A63B 2220/05* (2013.01); *A63B 2220/807* (2013.01)

(58) Field of Classification Search
CPC ...... G16H 20/30; G06T 7/251; A63B 24/0075
See application file for complete search history.

(56) References Cited

FOREIGN PATENT DOCUMENTS

KR   10-2097190 B1   4/2020

*Primary Examiner* — Kesha Frisby
(74) *Attorney, Agent, or Firm* — Harness, Dickey & Pierce, P.L.C.

(57) ABSTRACT

An AI motion recognition based smart hometraining platform is configured to include: a photographing unit; an motion image generation unit; a joint information generation unit; a deep learning determination unit determining whether the user motion is suitable by inputting user joint information; a correction information generation unit extracting correction information, and generating an image for a correction image or correction information based on the extracted correction information; a user image generation unit generating a user image acquired by overlaying a joint information image of the joint information generation unit to the user image; and a display displaying both the image for the correction message or the correction information and the user image of the user image generation unit in the display.

7 Claims, 7 Drawing Sheets

AI MOTION BASED SMART HOMETRAINING PLATFORM

FIELD

The present invention relates to an AI motion based smart hometraining platform for improving mild cognitive impairment.

BACKGROUND

As the related art, KR 10-2097190 (filed on Oct. 23, 2107) by Nam Jeong-wu, an application of a method for analyzing a real-time exercise motion by using a smart mirror and a smart mirror device therefore discloses a smart mirror for analyzing and displaying a real-time exercise motion, including an image sensor for acquiring an image related to an exercise motion; a body measurement unit for measuring a body size of a user based on the image acquired from the image sensor; a 3D model generation unit for generating a 3D musculoskeletal model of the user based on the measured body size; an exercise motion analysis unit estimating a joint position of the user based on the 3D musculoskeletal model, and recognizing the exercise motion based on estimation of the 3D musculoskeletal model; and a mirror unit for displaying a body image of the user rendered based on the recognized exercise motion, in which the body measurement unit recognizes a head, a body, an arm and a leg of the user based on joint position information used for each exercise motion and an image acquired though a basic motion inspection to measure lengths of two arms and two legs of the user, and measure circumferences of two arms and two legs of the user by using a distance measured based on silhouettes of a sagittal plane and a coronal plane of the user, and the measured joint position information.

KR 10-2414228 (filed on Nov. 27, 2019) by Park Dong-young discloses a mild cognitive impairment improvement system which provides contents for cognitive ability improvement through virtual reality, and provides next contents based on an answer for a question associated with the contents to gradually improve mild cognitive impairment by selecting patient customized contents.

SUMMARY

The present invention relates to an AI motion recognition based smart hometraining platform for improving old man mild cognitive impairment, which can coach posture correction and an effective exercise method through application of an AI based motion recognition technology and intuitive comparison with a training motion, construct an exercise of an exercise as a DB, and receive a feedback of professional opinions such as a cognitive function improvement degree, a future exercise prescription, etc. through consultation of medical and exercise experts.

Further, the present invention is to provide a smart hometraining technique for the elderly mild cognitive impairment improvement, which enable mutual communication among a user, an expert, and a guardian by checking a feedback result through a smart mirror and transmitting the feedback result to a mobile device of a guardian (including a child).

An exemplary embodiment of the present invention provides an AI motion recognition based smart hometraining platform including: a photographing unit 10 photographing an motion of a user and generating an motion image;

a deep learning determination unit 40 determining whether the user motion is suitable by inputting user joint information generated by the joint information generation unit 30 by using a prelearned deep learning determination model M with joint information of multiple users for a corresponding training motion as learning data;

a correction information generation unit 50 extracting correction information by comparing joint information of a trainer motion (a model motion for each type) and the joint information of the user motion, and generating an image for a correction image or correction information based on the extracted correction information;

a user image generation unit 60 generating a user image acquired by overlaying a joint information image of the joint information generation unit 30 to the user image; and a display 70 displaying both the image for the correction message or the correction information generated by the correction information generation unit 50 and the user image of the user image generation unit 60 in the display 70.

The AI motion cognitive based smart hometraining platform according to the present invention is preferably configured to further include a service providing server 80 receiving a user exercise history and a user exercise performing result from a server communication unit provided in a local device and transmitting the user exercise history and performing result to an expert terminal 90 and a guardian terminal 100; an expert terminal 90 presenting an exercise prescription by viewing the user exercise history and performing result from the service providing server 80; and a guardian terminal 100 receiving a report for the user exercise history and performing result.

In the AI motion cognitive based smart hometraining platform according to the present invention, the correction information generation unit 50 is constituted by a correction information extraction unit 51 extracting correction information for an error part and a correction message generation unit 55 visualizing the extracted correct information, and when the deep learning determination unit 40 determines that the user motion is unsuitable, the correction information extraction unit 51 selects the error part and extracts the correction information by comparing joint information of a training motion of a training motion information storage unit 55 and the joint information for the user motion provided by the joint information generation unit 30.

In the AI motion cognitive based smart hometraining platform according to the present invention, the correction message generation unit 55 may perform displaying a user error part in a training motion skeleton image, displaying the user error part in a training motion image, displaying the user error part in a user skeleton image, displaying the user error part in the user motion image, color expression or blink marking for the error part, or literal expression of correction information such as an error part correction angle by a voice transfer method of the correction information through a sound output unit 6.

In the AI motion cognitive based smart hometraining platform according to the present invention, it is preferable that the training motion as a motion for improving mild cognitive impairment or a dementia prevention motion includes a palm applause exercise using palms, such as vertical applause and horizontal applause for peripheral nerve and blood circulation promotion cognitive function enhancement, a both-arm exercise such as pushing both arms upward, forward, and sideward for brain balance and exercise ability cognitive function enhancement, and a full-body touch exercise that touches a head, a shoulder, and a hip with hands, and the joint information generation unit 30 generates positional information (2D coordinates or 3D coordinates) of a body, a shoulder joint, an elbow joint, a wrinkle joint, the head, etc., and the correction information extraction unit 51 uses adjacent joint angles (e.g., an angle between an upper arm and a lower arm) of the training motion and the user motion as parameters and compares a difference of the adjacent joint angles, and recognizes a corresponding part as the motion error part when a difference value of the angle is equal to or more than a threshold.

The AI motion cognitive based smart hometraining platform according to the present invention is configured to further include a sound input unit 5 generating a voice file by sensing a voice of a user; a voice recognition unit (not illustrated) recognizing a pronunciation of the recorded voice file and a voice determination unit (not illustrated) determining whether the voice of the user is suitable, the training motion further includes brain nerve gymnastics constituted by making a sound, pupil exercise, cheek tongue writing, patting a face and the head with the hands for simulating triple nerves, facial serves, glossopharyngeal nerves, and hypoglossal nerves through vocalization, and the joint information generation unit 30 preferably further generates positional information for at least 20 facial major spot points (non-resin major points) such as philtrum, lip, eye, noise, etc.

In the AI motion cognitive based smart hometraining platform according to the present invention, the service providing server 80 is configured to include a user database 81, an exercise evaluation unit 82, a level management unit 83, an expert exercise prescription unit 84, and a deep learning determination model learning unit 85, the user database 81 stores an exercise-specific performing history of the user, a cognitive impairment degree of the user, and an evaluation results of a motion for each type daily, weekly, and monthly, the exercise evaluation unit 82 determines whether the training motion is successfully performed by counting the number of errors determined by the deep learning determination unit 40, the level management unit 83 classifies and stores levels into a basic level, a middle level, and a high level for the evaluation result of the exercise evaluation unit 82, the expert exercise prescription unit 84 expresses training motion information recommended by the expert terminal 90 through the display 70 or an sound output unit 6, and the deep learning determination model learning unit 85 trains a model by using motions and determination results of various users as learning data.

According to the present invention, provided is an AI motion recognition based smart hometraining platform for improving old man mild cognitive impairment, which can coach posture correction and an effective exercise method through application of an AI based motion recognition technology and intuitive comparison with a training motion, construct an exercise of an exercise as a DB, and receive a feedback of professional opinions such as a cognitive function improvement degree, a future exercise prescription, etc. through consultation of medical and exercise experts.

Further, according to the present invention, provided is a smart hometraining technique for the elderly mild cognitive impairment improvement, which enable mutual communication among a user, an expert, and a guardian by checking a feedback result through a smart mirror and transmitting the feedback result to a mobile device of a guardian (including a child).

DETAILED DESCRIPTION

Figure 1:
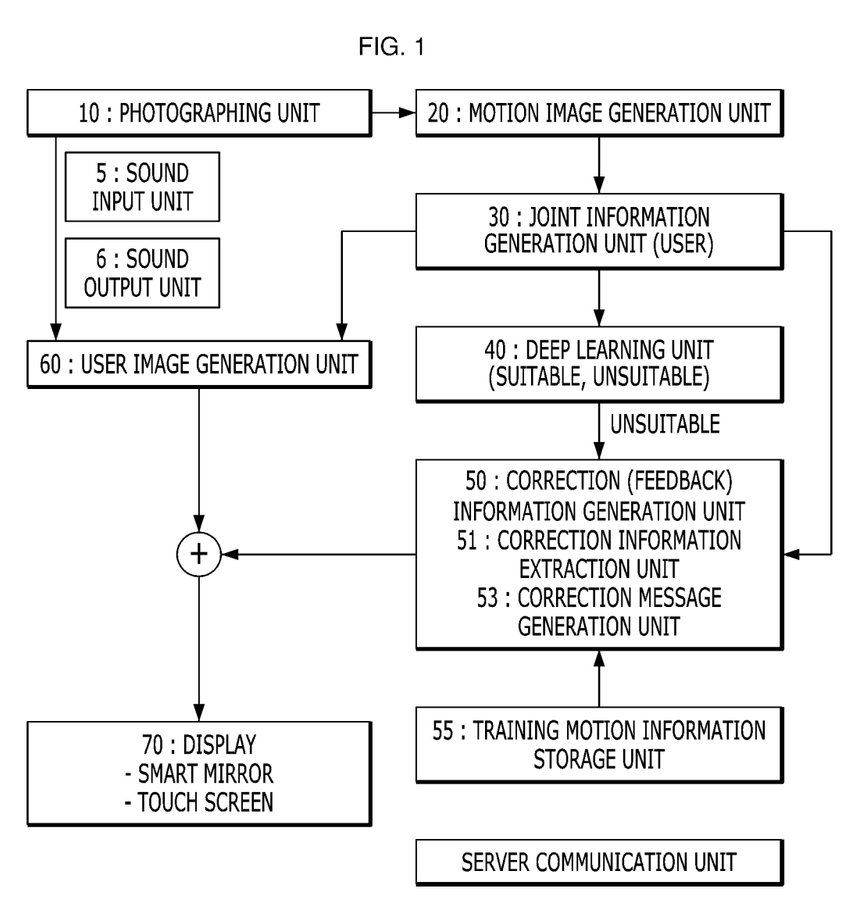
FIG. 1 is a total configuration diagram of an AI motion cognitive based smart hometraining platform according to the present invention.
Figure 2:
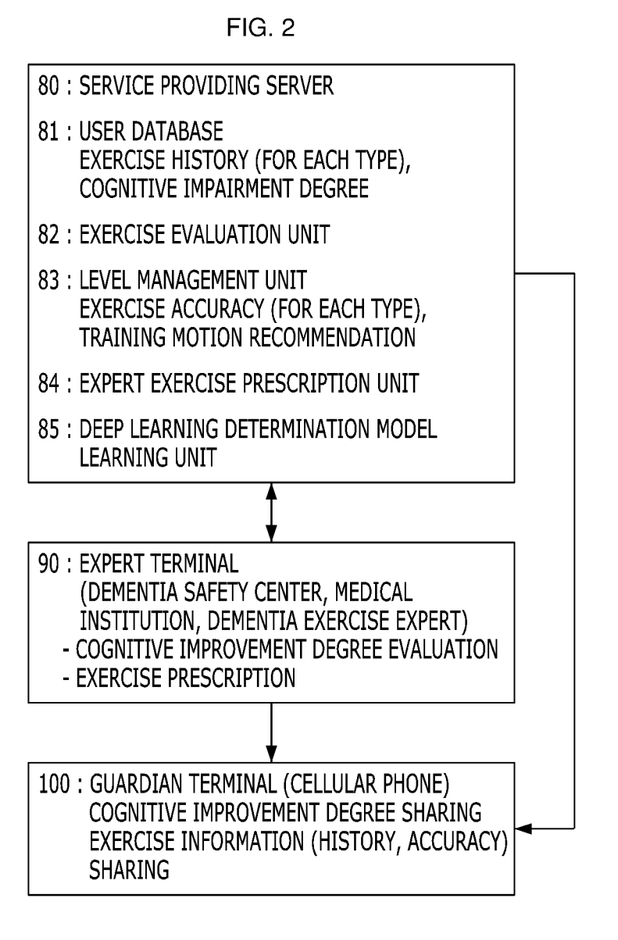
FIG. 2 is a total configuration diagram of an AI motion cognitive based smart hometraining platform according to the present invention (a server, an expert, terminal, and a guardian terminal).
Figure 3:
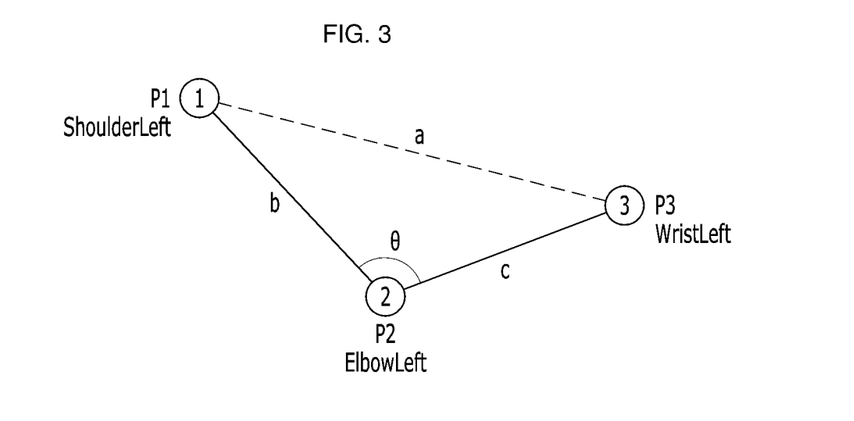
FIG. 3 is an exemplary diagram of a joint point calculation according to the present invention.
Figure 4:
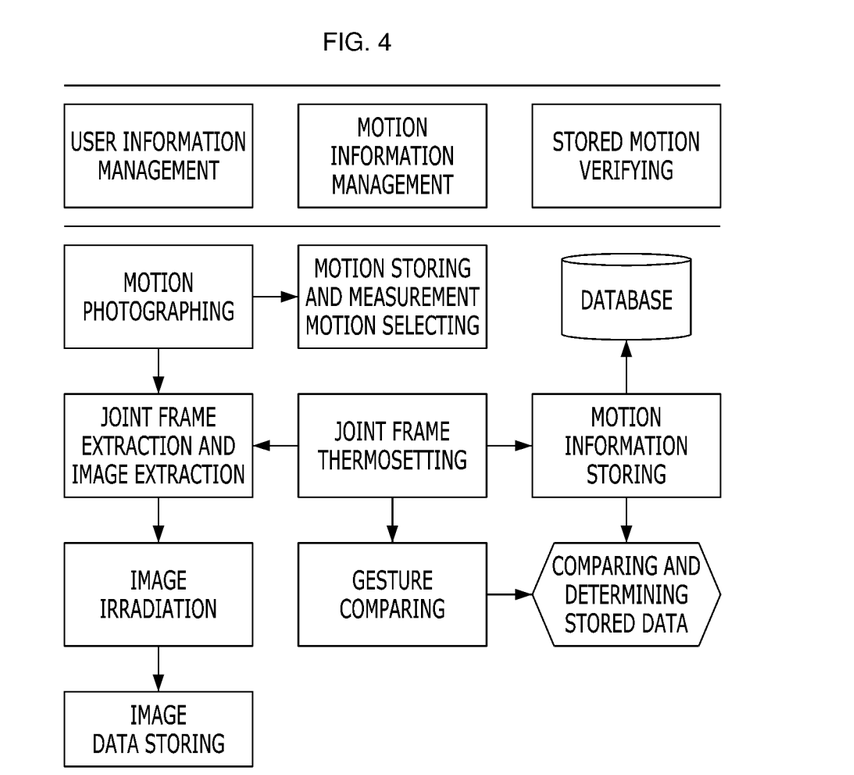
FIGS. 4, 5, and 6 are an explanatory diagram of an AI motion cognitive based smart hometraining platform according to the present invention.
Figure 5:
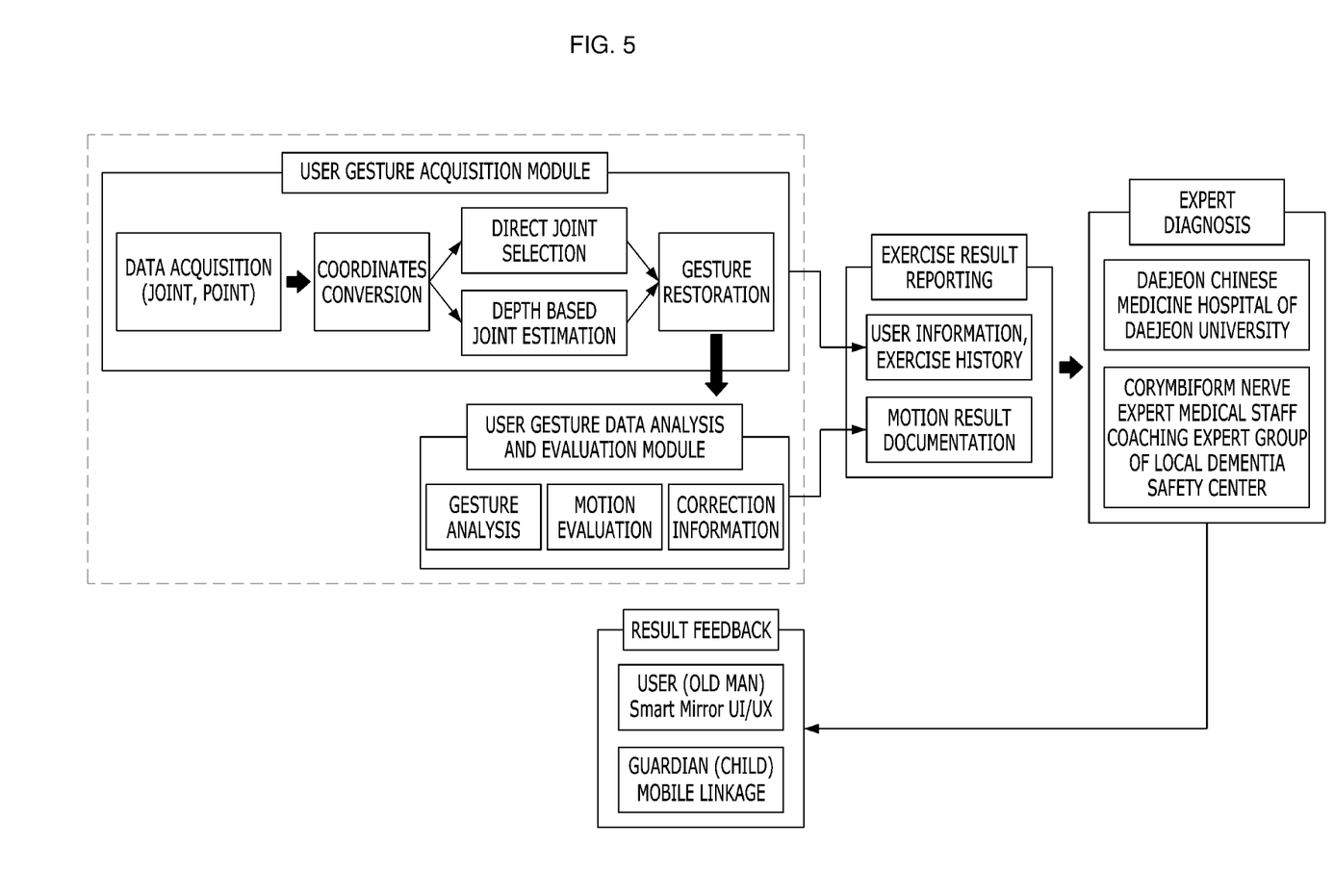
Figure 6:
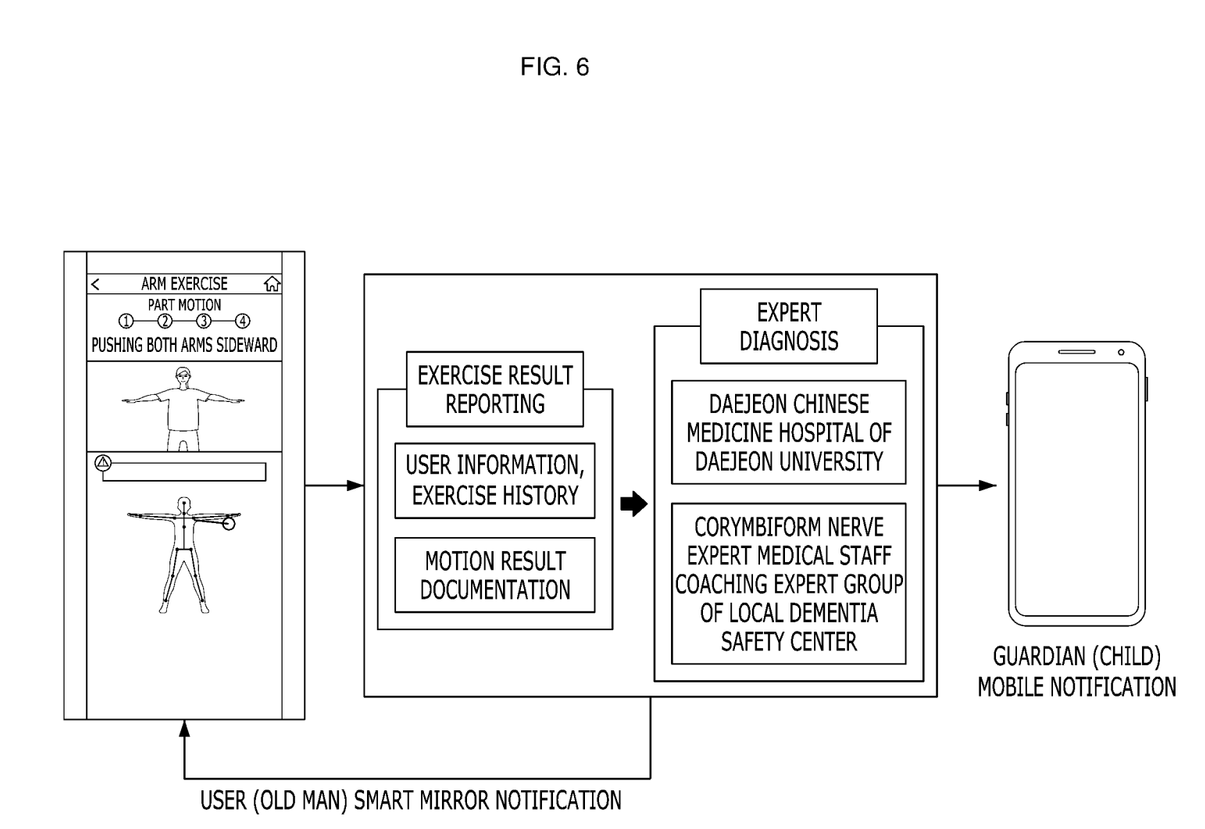
Figure 7:
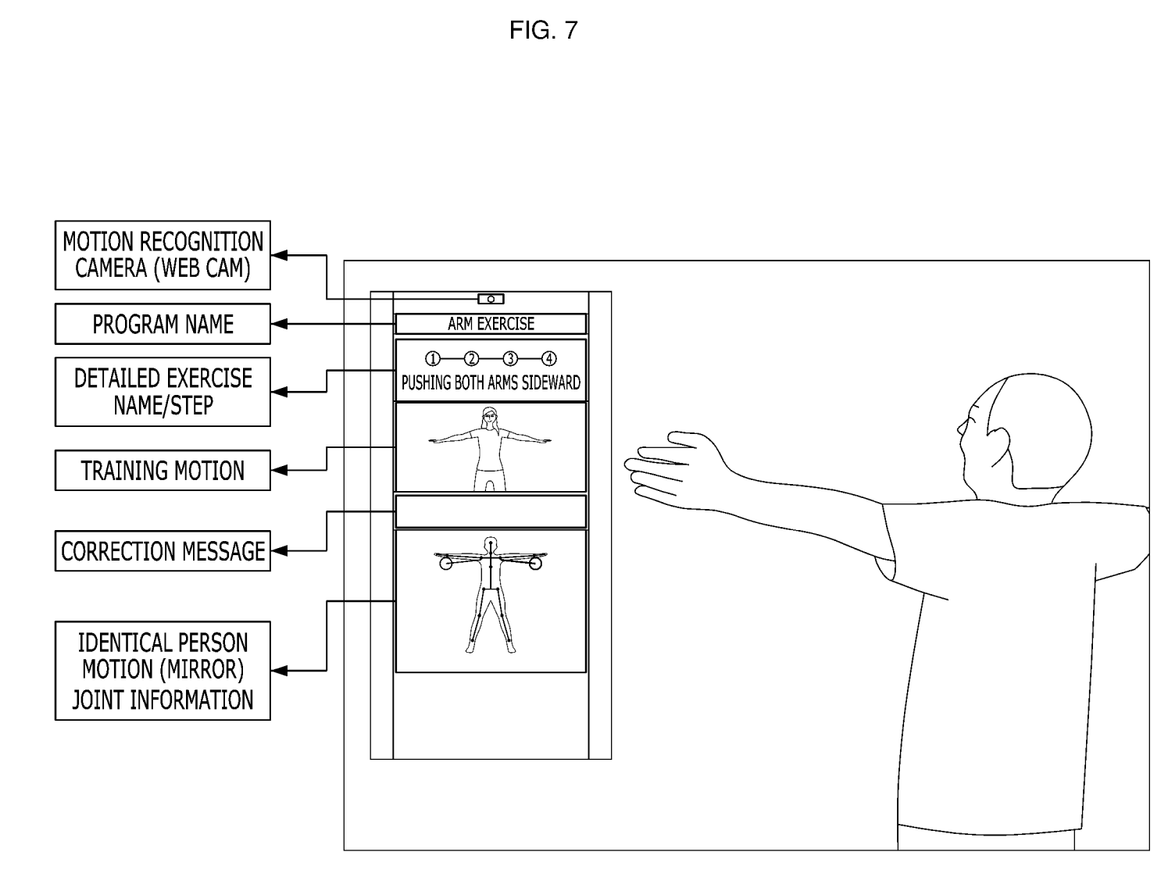
FIG. 7 is an explanatory diagram of a use state of an AI motion cognitive based smart hometraining platform according to the present invention.
Figure 8:
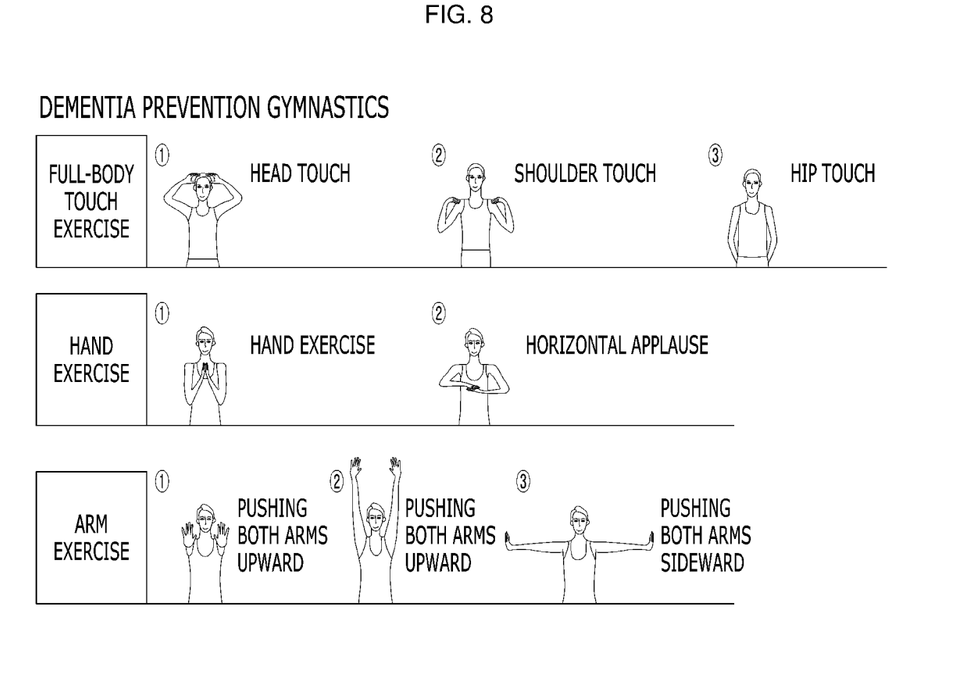
FIG. 8 illustrates an exemplary embodiment of a mild cognitive impairment enhancement training motion.

Hereinafter, an AI motion cognitive based smart hometraining platform according to the present invention will be described in detail with reference to the accompanying drawings. FIG. 1 is a total configuration diagram of an AI motion cognitive based smart hometraining platform according to the present invention, FIG. 2 is a total configuration diagram of an AI motion cognitive based smart hometraining platform according to the present invention (a server, an expert, terminal, and a guardian terminal), FIG. 3 is an exemplary diagram of a joint point calculation according to the present invention, FIGS. 4, 5, and 6 are an explanatory diagram of an AI motion cognitive based smart hometraining platform according to the present invention, FIG. 7 is an explanatory diagram of a use state of an AI motion cognitive based smart hometraining platform according to the present invention, and FIG. 8 illustrates an exemplary embodiment of a mild cognitive impairment enhancement training motion.

As illustrated in FIGS. 1, 4, 5, and 6, the AI motion cognitive based smart hometraining platform according to the present invention includes a photographing unit 10, a motion image generation unit 20, a joint information generation unit 30, a deep learning determination unit 40, a correction information generation unit 50, a user image generation unit 60, and a display 70.

The photographing unit 10 generates a motion image by photographing a motion of a user. The photographing unit 10 may be a general 2D camera, a 3D depth camera, and a web camera. For more accurate 3D coordinate extraction, a plurality of cameras may be used.

The motion image generation unit 20 generates a frame-specific image (image, $I_k$, k=0, −1, −2, . . . , k represents a discrete time) from the motion image at a predetermine time interval (e.g., $\Delta T1=1/1{\sim}10$ sec, for each frame).

The joint information generation unit 30 extracts a joint point for each frame based on the user image, and generates positional information (2D coordinates or 3D coordinates ($X_{ki}$, $Y_{ki}$, $Z_{ki}$)) of each joint point.

The deep learning determination unit 40 determines whether the user motion is suitable by inputting user joint information generated by the joint information generation unit 30 by using a prelearned deep learning determination model M with joint information of multiple users for a corresponding training motion as learning data.

The correction information generation unit 50 extracts correction information by comparing joint information of a trainer motion (a model motion for each type) and the joint information of the user motion, and generates an image for a correction image or correction information based on the extracted correction information.

The user image generation unit 60 generates a user image acquired by overlaying a joint information image of the joint information generation unit 30 to the user image.

The display 70 displays both the image for the correction message or the correction information generated by the correction information generation unit 50 and the user image of the user image generation unit 60 in the display 70. The display 70 may be a smart mirror that has a mirror function upon off and performs a display function upon use. The display further has a touch screen function to facilitate an interface of a user who is not familiar with an old man and an electronic device.

As illustrated in FIG. 2, the AI motion cognitive based smart hometraining platform according to the present invention is preferably configured to further include a service providing server 80 receiving a user exercise history and a user exercise performing result from a server communication unit provided in a local device and transmitting the user exercise history and performing result to an expert terminal 90 and a guardian terminal 100; an expert terminal 90 presenting an exercise prescription by viewing the user exercise history and performing result from the service providing server 80; and a guardian terminal 100 receiving a report for the user exercise history and performing result.

As illustrated in FIGS. 1 and 7, in the AI motion cognitive based smart hometraining platform according to the present invention, the correction information generation unit 50 is constituted by a correction information extraction unit 51 extracting correction information for an error part and a correction message generation unit 55 visualizing the extracted correct information, and when the deep learning determination unit 40 determines that the user motion is unsuitable, the correction information extraction unit 51 selects the error part and extracts the correction information by comparing joint information of a training motion of a training motion information storage unit 55 and the joint information for the user motion provided by the joint information generation unit 30.

As illustrated in FIGS. 6 and 7, in the AI motion cognitive based smart hometraining platform according to the present invention, the correction message generation unit 55 may perform displaying a user error part in a training motion skeleton image, displaying the user error part in a training motion image, displaying the user error part in a user skeleton image, displaying the user error part in the user motion image, color expression or blink marking for the error part, or literal expression of correction information such as an error part correction angle by a voice transfer method of the correction information through a sound output unit 6.

As illustrated in FIG. 8, in the AI motion cognitive based smart hometraining platform according to the present invention, the training motion as a motion for improving mild cognitive impairment or a dementia prevention motion may include a palm applause exercise using palms, such as vertical applause and horizontal applause for peripheral nerve and blood circulation promotion cognitive function enhancement, a both-arm exercise such as pushing both arms upward, forward, and sideward for brain balance and exercise ability cognitive function enhancement, and a full-body touch exercise that touches a head, a shoulder, and a hip with hands.

Here, as illustrated in FIG. 3, it is preferable that the joint information generation unit 30 generates positional information (2D coordinates or 3D coordinates) of a body, a shoulder joint, an elbow joint, a wrinkle joint, the head, etc., and the correction information extraction unit 51 uses adjacent joint angles (e.g., an angle between an upper arm and a lower arm) of the training motion and the user motion as parameters and compares a difference of the adjacent joint angles, and recognizes a corresponding part as the motion error part when a difference value of the angle is equal to or more than a threshold.

As illustrated in FIG. 1, the AI motion cognitive based smart hometraining platform according to the present invention is configured to further include a sound input unit 5 generating a voice file by sensing a voice of a user; a voice recognition unit (not illustrated) recognizing a pronunciation of the recorded voice file and a voice determination unit (not illustrated) determining whether the voice of the user is suitable, wherein the training motion further includes brain nerve gymnastics constituted by making a sound, pupil exercise, cheek tongue writing, patting a face and the head with the hands for simulating triple nerves, facial serves, glossopharyngeal nerves, and hypoglossal nerves through vocalization, and the joint information generation unit 30 preferably further generates positional information for at least 20 facial major spot points (non-resin major points) such as philtrum, lip, eye, noise, etc.

As illustrated in FIG. 2, in the AI motion cognitive based smart hometraining platform according to the present invention, the service providing server 80 is configured to include a user database 81, an exercise evaluation unit 82, a level management unit 83, an expert exercise prescription unit 84, and a deep learning determination model learning unit 85, the user database 81 stores an exercise-specific performing history of the user, a cognitive impairment degree of the user, and an evaluation results of a motion for each type daily, weekly, and monthly, the exercise evaluation unit 82 determines whether the training motion is successfully performed by counting the number of errors determined by the deep learning determination unit 40, the level management unit 83 classifies and stores levels into a basic level, a middle level, and a high level for the evaluation result of the exercise evaluation unit 82, the expert exercise prescription unit 84 expresses training motion information recommended by the expert terminal 90 through the display 70 or an sound output unit 6, and the deep learning determination model learning unit 85 trains a model by using motions and determination results of various users as learning data.

<Methodical Description>

A performing process of an AI motion cognitive based smart hometraining platform according to the present invention is as follows. In a motion photographing step (S10), the photographing unit 10 generates a motion image by photographing a motion of a user. Next, in a frame-specific image generating step (S20), the motion image generation unit 20 generates a frame-specific image (image, $I_k$, k=0, −1, −2, . . . , k represents a discrete time) from the motion image at a predetermine time interval (e.g., ΔT1=1/1~10 sec, for each frame).

In a user joint information generating step (S30), the joint information generation unit 30 extracts a joint point for each frame based on the user image, and generates positional information (2D coordinates or 3D coordinates ($X_{ki}$, $Y_{ki}$, $Z_{ki}$)) of each joint point.

In a suitability determining step (S40), a deep learning determination unit 40 prelearned by using a prelearned deep learning determination model M with joint information of multiple users for a corresponding training motion as learning data determines whether the user motion is suitable by inputting user joint information generated by the joint information generation unit 30.

In a correction information generating step (S50), the correction information generation unit 50 extracts correction information by comparing joint information of a trainer motion (a model motion for each type) and the joint information of the user motion, and generates an image for a correction image or correction information based on the extracted correction information.

In a user image generating step (S60), the user image generation unit 60 generates a user image acquired by overlaying a joint information image of the joint information generation unit 30 to the user image.

In a display step (S70), the display 70 displays both the image for the correction message or the correction information generated in the correction information generating step (S50) and the user image in the user image generating step (S60).

In a transmitting step (S80), the service providing server 80 receives a user exercise history and a user exercise performing result from a server communication unit provided in a local device and transmits the user exercise history and performing result to an expert terminal 90 and a guardian terminal 100. Last, in an expert prescription presenting step (S90), the expert terminal 90 presents an exercise prescription by viewing the user exercise history and performing result from the service providing server 80.

An AI motion cognitive based smart hometraining platform providing method is configured to include a guardian reporting step (S100) in which the guardian terminal 100 receives a user exercise history and a performing result from the service providing server 80.

Although the present invention has been described in connection with the preferred embodiments mentioned above, the scope of the present invention is not limited to this embodiment, and the scope of the present invention is determined by the following claims and will include various modifications and variations.

The reference numerals described in the following claims are simply to assist understanding of the invention, so that it is apparent that the reference numerals do not affect the analysis of the scope of the rights and the scope of the rights should not be interpreted to be narrow by the described reference numerals.

What is claimed is:

1. An AI motion recognition based smart hometraining platform for enhancing mild cognitive impairment, comprising:
    a photographing unit photographing a motion of a user and generating an motion image;
    an motion image generation unit generating a frame-specific image (image, $I_k$, k=0, −1, −2, . . . , k represents a discrete time) from the motion image at a predetermine time interval (e.g., ΔT1=1/1~10 sec, for each frame);
    a joint information generation unit extracting a joint point for each frame based on the user image, and generating positional information (2D coordinates or 3D coordinates ($X_{ki}$, $Y_{ki}$, $Z_{ki}$)) of each joint point;
    a deep learning determination unit determining whether the user motion is suitable by inputting user joint information generated by the joint information generation unit by using a prelearned deep learning determination model M with joint information of multiple users for a corresponding training motion as learning data;
    a correction information generation unit extracting correction information by comparing joint information of a trainer motion (a model motion for each type) and the joint information of the user motion, and generating an image for a correction image or correction information based on the extracted correction information;
    a user image generation unit generating a user image acquired by overlaying a joint information image of the joint information generation unit to the user image; and
    a display displaying both the image for the correction message or the correction information generated by the correction information generation unit and the user image of the user image generation unit in the display.

2. The AI motion recognition based smart hometraining platform for enhancing mild cognitive impairment of claim 1, further comprising:
    a service providing server receiving a user exercise history and a user exercise performing result from a server communication unit provided in a local device and transmitting the user exercise history and performing result to an expert terminal and a guardian terminal;
    an expert terminal presenting an exercise prescription by viewing the user exercise history and performing result from the service providing server; and
    a guardian terminal receiving a report for the user exercise history and performing result.

3. The AI motion recognition based smart hometraining platform for enhancing mild cognitive impairment of claim 2, wherein the correction information generation unit is constituted by a correction information extraction unit extracting correction information for an error part and a correction message generation unit visualizing the extracted correct information, and
    when the deep learning determination unit determines that the user motion is unsuitable, the correction information extraction unit selects the error part and extracts the correction information by comparing joint information of a training motion of a training motion information storage unit and the joint information for the user motion provided by the joint information generation unit.

4. The AI motion recognition based smart hometraining platform for enhancing mild cognitive impairment of claim 3, wherein the correction message generation unit performs displaying a user error part in a training motion skeleton image, displaying the user error part in a training motion image, displaying the user error part in a user skeleton image, displaying the user error part in the user motion image, color expression or blink marking for the error part, or literal expression of correction information such as an error part correction angle by a voice transfer method of the correction information through a sound output unit.

5. The AI motion recognition based smart hometraining platform for enhancing mild cognitive impairment of claim 3, wherein the training motion as a motion for improving mild cognitive impairment or a dementia prevention motion includes:
- a palm applause exercise using palms, such as vertical applause and horizontal applause for peripheral nerve and blood circulation promotion cognitive function enhancement,
- a both-arm exercise such as pushing both arms upward, forward, and sideward for brain balance and exercise ability cognitive function enhancement, and
- a full-body touch exercise that touches a head, a shoulder, and a hip with hands, and
- the joint information generation unit generates positional information (2D coordinates or 3D coordinates) of a body, a shoulder joint, an elbow joint, a wrinkle joint, the head, etc., and
- the correction information extraction unit uses adjacent joint angles (e.g., an angle between an upper arm and a lower arm) of the training motion and the user motion as parameters and compares a difference of the adjacent joint angles, and recognizes a corresponding part as the motion error part when a difference value of the angle is equal to or more than a threshold.

6. The AI operation recognition based smart hometraining platform for enhancing mild cognitive impairment of claim 2, further comprising:
- a sound input unit generating a voice file by sensing a voice of a user;
- a voice recognition unit recognizing a pronunciation of the recorded voice file and
- a voice determination unit (not illustrated) determining whether the voice of the user is suitable, wherein the training motion further includes brain nerve gymnastics constituted by making a sound, pupil exercise, cheek tongue writing, patting a face and the head with the hands for simulating triple nerves, facial serves, glossopharyngeal nerves, and hypoglossal nerves through vocalization, and
the joint information generation unit further generates positional information for at least facial major spot points (non-resin major points) such as philtrum, lip, eye, noise, etc.

7. The AI operation recognition based smart hometraining platform for enhancing mild cognitive impairment of claim 2, wherein the service providing server is configured to include a user database, an exercise evaluation unit, a level management unit, an expert exercise prescription unit, and a deep learning determination model learning unit,
- the user database stores an exercise-specific performing history of the user, a cognitive impairment degree of the user, and an evaluation results of a motion for each type daily, weekly, and monthly,
- the exercise evaluation unit determines whether the training motion is successfully performed by counting the number of errors determined by the deep learning determination unit,
- the level management unit classifies and stores levels into a basic level, a middle level, and a high level for the evaluation result of the exercise evaluation unit,
- the expert exercise prescription unit expresses training motion information recommended by the expert terminal through the display or an sound output unit, and
- the deep learning determination model learning unit trains a model by using motions and determination results of various users as learning data.

* * * * *